US006254639B1

(12) United States Patent
Peckitt

(10) Patent No.: US 6,254,639 B1
(45) Date of Patent: Jul. 3, 2001

(54) PROSTHETIC IMPLANTS

(76) Inventor: Ninian Peckitt, St. Chad's House, Hooton Pagnell, Doncaster DN5 7BW (GB)

( * ) Notice: Subject to any disclaimer, the term of this patent is extended or adjusted under 35 U.S.C. 154(b) by 0 days.

(21) Appl. No.: 09/269,291

(22) PCT Filed: Sep. 25, 1997

(86) PCT No.: PCT/GB97/02620

§ 371 Date: May 27, 1999

§ 102(e) Date: May 27, 1999

(87) PCT Pub. No.: WO98/12995

PCT Pub. Date: Apr. 2, 1998

(30) Foreign Application Priority Data

Sep. 25, 1996 (GB) .................................................. 9619943

(51) Int. Cl.[7] .................................................. A61F 2/02
(52) U.S. Cl. ........................................ 623/11.11; 623/901
(58) Field of Search ............................... 623/901, 16, 23, 623/11.11, 16.11, 17.17, 17.18, 18.11, 17.19; 364/468.24, 468.25, 468.27

(56) References Cited

U.S. PATENT DOCUMENTS

| 4,506,393 | * | 3/1985 | Murphy | 128/898 |
|---|---|---|---|---|
| 4,895,573 | * | 1/1990 | Koeneman et al. | 623/23 |
| 4,936,862 | * | 6/1990 | Walker et al. | 623/23 |
| 5,041,141 | * | 8/1991 | Ypma et al. | 623/23 |
| 5,156,777 | | 10/1992 | Kaye . | |
| 5,218,427 | | 6/1993 | Koch . | |
| 5,301,117 | * | 4/1994 | Riga | 623/901 |
| 5,360,446 | * | 11/1994 | Kennedy | 623/901 |
| 5,370,692 | * | 12/1994 | Fink et al. | 623/901 |
| 5,798,924 | * | 8/1998 | Eufinger et al. | 364/468.24 |
| 5,824,083 | * | 10/1998 | Draenert | 623/901 |
| 5,857,853 | * | 1/1999 | Van Nifterick et al. | 433/213 |

FOREIGN PATENT DOCUMENTS

| 43 41 367 C1 | 6/1995 | (DE) . | |
|---|---|---|---|
| 0 097 001 A1 | 12/1983 | (EP) . | |
| 0 574 098 A1 | 12/1993 | (EP) . | |
| 0 622 052 A1 | 11/1994 | (EP) . | |
| 9107139 | * 5/1991 | (WO) | 623/901 |
| 95/07509 | 3/1995 | (WO) . | |

* cited by examiner

Primary Examiner—Jeffrey A. Smith
Assistant Examiner—Eduardo C. Robert
(74) Attorney, Agent, or Firm—Ratner & Prestia

(57) ABSTRACT

A prosthetic implant to replace damaged or diseased bone, especially in the maxillofacial region, is produced by producing a digital representation of the region of interest by CAT scan, using the data to create a model by stereolithography, and using the data also to produce the implant by CNC machining. The implant is an entire replacement extracts excised surgically, without need for reconstructing bone or soft tissue.

16 Claims, 6 Drawing Sheets ered from bone in other parts of the patient's body. In either case, it is then necessary to attempt to reform the adjacent soft tissue over the resulting implant.
PROSTHETIC IMPLANTS

BACKGROUND OF THE INVENTION

1. Field of the Invention

This invention relates to an improved method of making prosthetic implants, methods of treatment incorporating the use of such implants, and to the prosthetic implants themselves.

The invention is of particular usefulness in relation to maxillofacial surgery and will be particularly described with reference to that field, but may also be utilised in the treatment of disease or damage in other parts of the body.

2. Prior Art

Maxillofacial surgery may be necessary to deal with congenital defect, accidental damage, or malignant tumours. Such surgery presents particular difficulties since the aim is to achieve a result which is not only functional in dealing with the particular problem addressed, but also ensures that a patient is left with a good level of ability to breath, eat and speak, while at the same time achieving a satisfactory aesthetic appearance.

Techniques are known in which diseased or damaged bone is excised and replaced. The replacement may be by way of grafting bone taken from other parts of the patient's body. More recently replacement bone has been achieved by attaching a titanium armature to sound bone to act as a support for grafted bone cells derived from bone in other parts of the patient's body. In either case, it is then necessary to attempt to reform the adjacent soft tissue over the resulting implant.

Another known technique is the use of microvascular free transfer osseofasciocutaneous flaps, in which a flap of bone and skin, for example from the forearm and optionally with attached muscle, is transferred to the mouth, with the blood vessels of the flap being connected to those of the head by microscopic surgery. A functional result may be achieved, but is non-anatomical.

Such techniques are extremely time consuming and difficult. A typical maxillofacial repair may require a surgical procedure lasting up to about 15 hours, and the procedure will involve opening a second surgical site (typically in the region of the iliac crest) to obtain bone or bone cells for grafting.

OBJECTS OF THE INVENTION

An object of the present invention is to enable reconstructive surgery of this nature to be carried out much more rapidly, thus markedly reducing the stress on the patient caused by the surgery, while reducing the load on the surgical team and also markedly reducing the costs of the surgery.

BRIEF SUMMARY OF THE INVENTION

In accordance with one aspect of the present invention, a method of making a prosthetic implant comprises the steps of obtaining a set of data defining the body parts of interest in three dimensions, using said set of data to create a three dimensional model of at least part of the body parts of interest, and using the three dimensional model to develop and fit to size a prosthetic implant which entirely replaces body parts which are missing or are to be excised from the patient.

The invention also provides a prosthesis made by the foregoing method.

From another aspect, the invention provides a method of treating damaged, diseased or missing body parts which comprises excising damaged and/or diseased body parts and selected adjacent parts, and replacing excised and/or missing parts entirely by a prosthetic implant secured to the sound adjacent bone structures. In the preferred form of the method, both bone and soft tissue are replaced by a single prosthetic implant made of a material onto the surface of which soft tissue is capable of growing in a manner to prevent the incursion of infection; such a material will typically be titanium.

The foregoing method in preferably carried out by obtaining a set of data defining the body parts of interest in three dimensions, using said set of data to create a three dimensional model of at least part of the body parts of interest, and using the model to develop and fit to size the prosthetic implant prior to surgery.

In preferred forms of the invention the prosthesis extends through a body surface such as skin or mucous membrane, for example in the palate or nasal cavity.

The prosthetic implant may be provided with mechanical attachment means for the releasable attachment of further prosthetic devices such as dentures.

The set of data defining the body parts of interest is preferably reduced by CAT scanning. The data resulting from the CAT scanning may be manipulated by computer, for example to derive from a CAT head scan a set of data defining three dimensionally only the bony structures of the skull.

The three dimensional model may conveniently be produced by stereolithography in a manner known per se by laser irradiation of a photoreactive polymer.

A further aspect of the invention provides a connector block comprising a body and a post extending from the body, the post being shaped for selective attachment to dental prostheses, and the body being formed with passages for rivets for attachment to a surgical plate.

Preferably, the body is rectangular, and the connector block is formed integrally from titanium.

DETAILED DESCRIPTION OF THE INVENTION

Embodiments of the invention will now be described, by way of example only, with reference to the drawings, in which.

Figure 1:
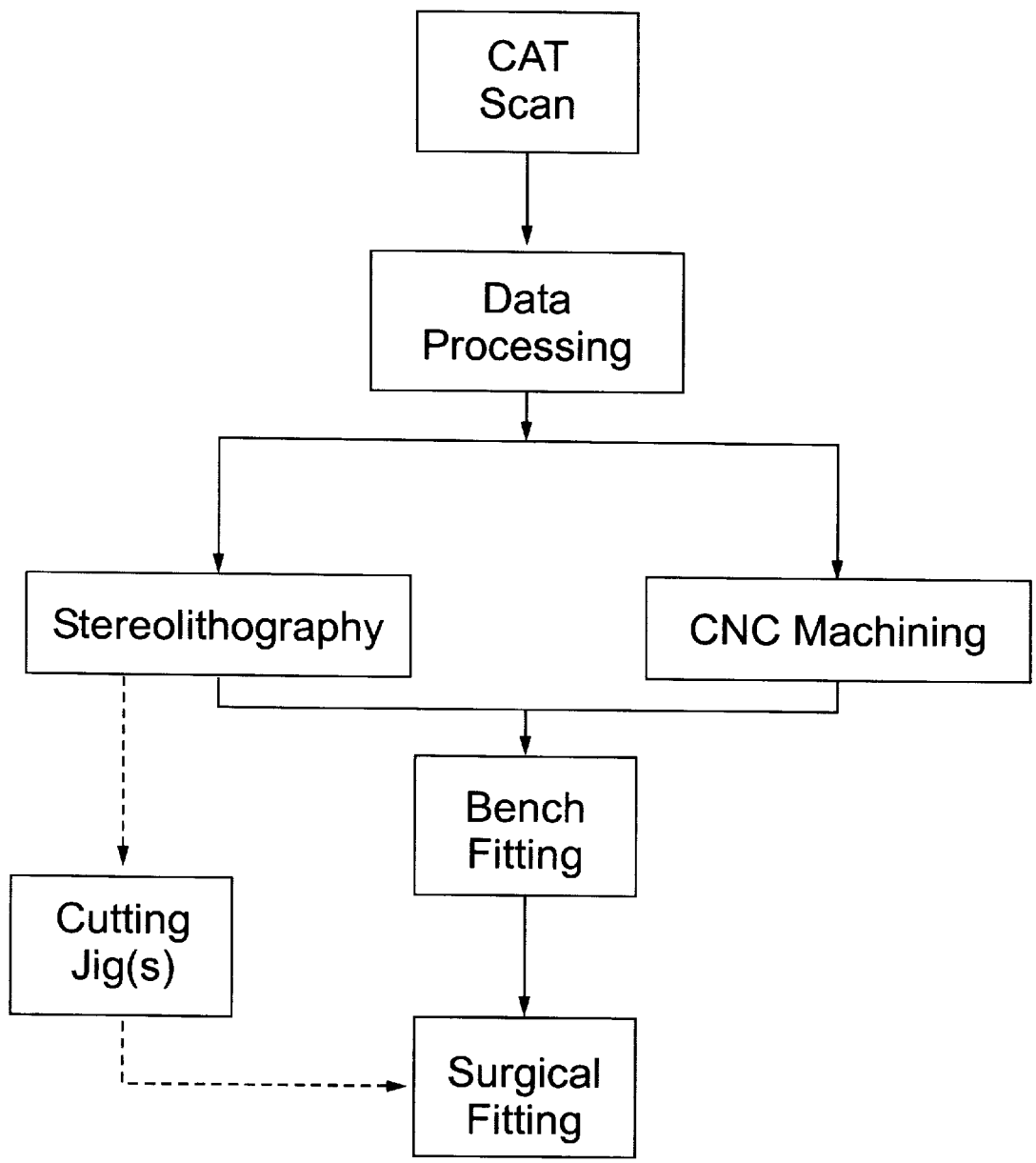
FIG. 1 is a flow chart illustrating the method of the present invention.

Referring to FIG. 1, the process of the present invention is based upon the use of a CAT scan to derive a set of data defining in three dimensions the body part of interest, for example the skull. Accordingly, a conventional CAT scan provides data to a data processing step in which the data defining the bony structures are retained and the soft structure data discarded.

The processed data is then used to produce a replica of the patient's skull by stereolithography. There are techniques well known per se for the production of three dimensional models from digital data by stereolithography by laser irradiation of a bath of photoreactive polymer. In this way, a model of the patient's skull in its existing form is obtained.

The data from the CAT scan can also be processed to provide a further set of data defining in three dimensions a desired replacement part. This further data is then used to produce a replacement part by CNC machining from solid titanium.

At this stage, the surgical team have a true scale model of the existing skull plus a machined replacement for part of the skull. These can be used in the workshop (that is, in non-surgical, non-sterile conditions) to refine the surgical operation to be performed. In particular, the surgeon can plan the best positions to cut to obtain sound bone on which to mount the implant. The cutting and mounting can be performed experimentally on the model skull, and the shape of the machined implant can be refined in this process.

Optionally, as indicated in FIG. 1, during the workshop stage cutting jigs may be produced which are located with respect to well-defined points on the skull and provide a guide to enable the surgeon to cut the bone accurately in the planned planes.

Once the surgical plan and prosthetic implant have been refined in the workshop, the prosthesis is implanted surgically in the conventional manner. Typically, the prosthesis will be secured to sound bone by means of bone screws or expansion-type fixings.

An important feature of the present invention is that the prosthesis is of a material, typically titanium, which is compatible with passing through the surface of soft tissue without permitting the ingress of infection along the exposed surface of the implant. This allows the prosthesis to be a complete replacement for excised parts.

For example, in the case where part of the upper or lower jaw or the palate must be removed, the parts removed are replaced only by the implant, without attempting to separate and then reposition the soft tissue of the gum or palate. This is not only much less time consuming in surgery, but also makes the surgical site functional much more quickly post-operatively.

Figure 2A:
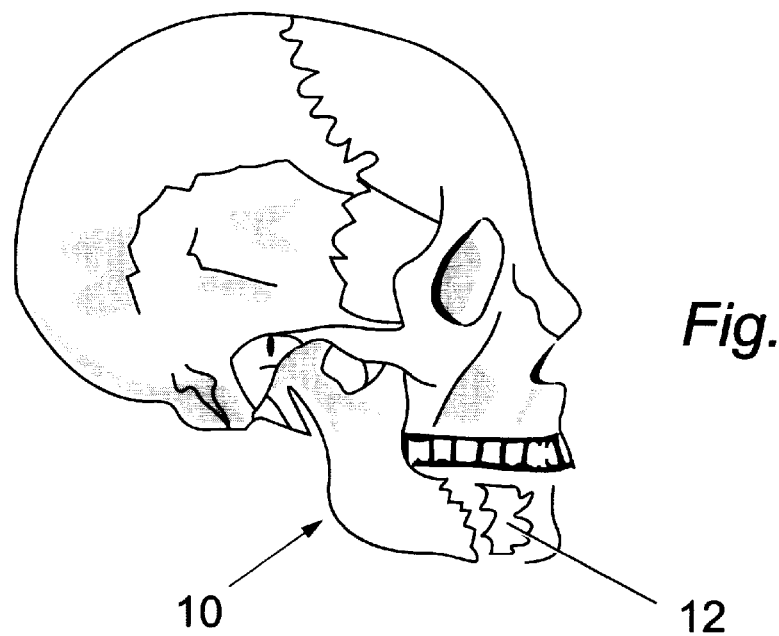
FIGS. 2a and 2b are schematic views in side and front views respectively of a skull having an area of damage in the lower jaw.
Figure 2B:
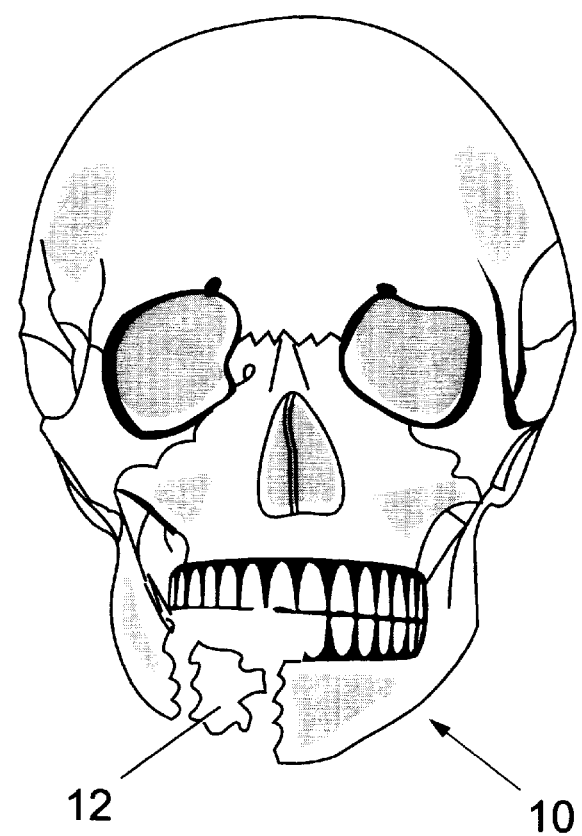
Figure 3A:
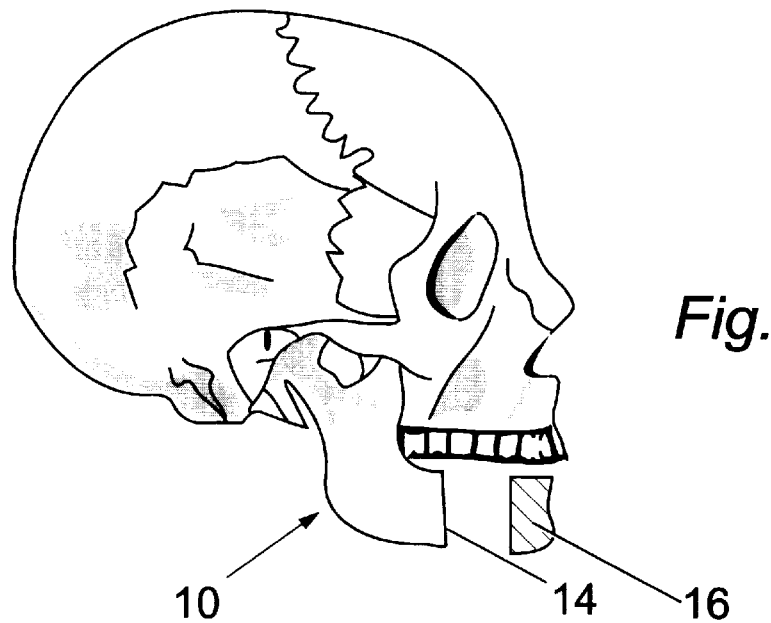
FIGS. 3a and 3b are similar view of the skull with the damaged area excised.
Figure 3B:
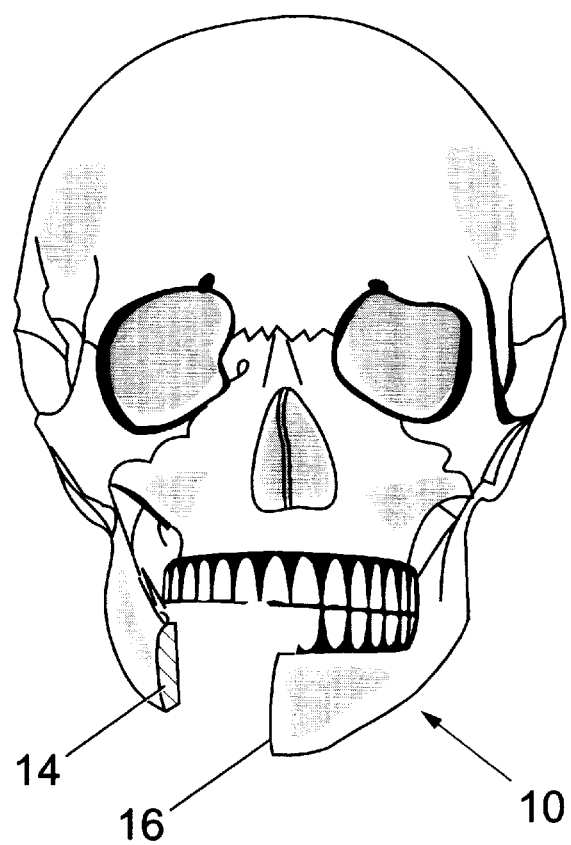
Figure 4A:
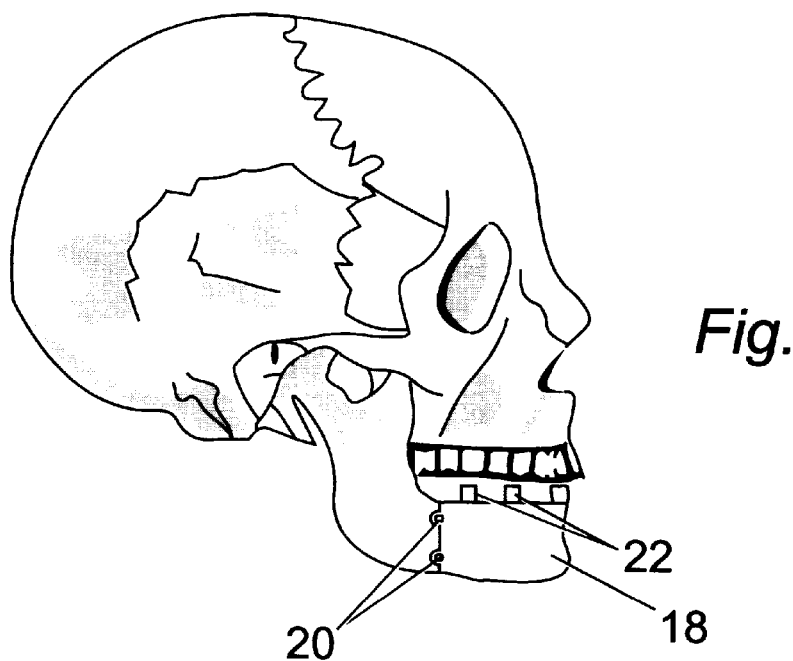
FIGS. 4a and 4b are similar views of the same skull with a prosthesis implanted.
Figure 4B:
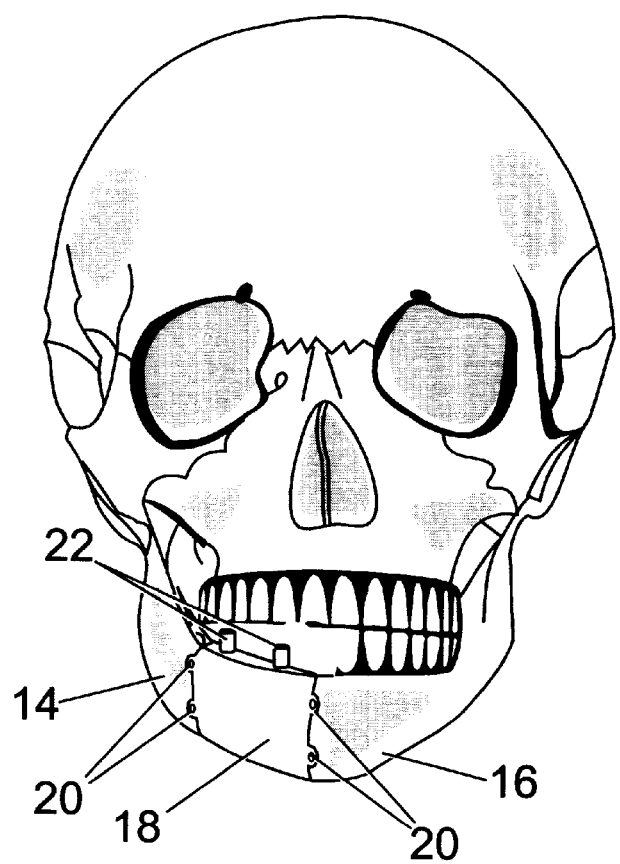

FIGS. 2 to 4 illustrate such a procedure schematically with reference to a damaged lower mandible.

As seen in FIG. 2 a lower jaw 10 has an area of damage 12 involving both the jaw and the teeth. FIG. 3 illustrates the damaged area cut back to sound bone at 14 and 16. In FIG. 4, a solid implant 18 of titanium has been attached to the sound bone areas 14, 16 by bone screws 20. The implant 18 is provided with posts 22 to which a denture may be directly mounted. It will be understood that the implant 18 extends into the interior of the patient's mouth, within which it will be visible, and the margin of the healthy, non-excised gum will grow onto the surface of the implant.

The stages of FIGS. 2 to 4 will be carried through first in the workshop on the model skull, and only thereafter on the patient surgically.

For simplicity of description, FIG. 4 shows the implant 18 being attached by simple bone screws 20. In View of the loads typically placed on the mandible, it is preferable to obtain a more secure mechanical engagement. One such arrangement is illustrated in FIG. 5. The implant 18 is secured (for example, rivetted or welded) to a plate 24 which in turn is attached to the sound bone areas 14, 16, to lie along the underside of the mandible. The example shown makes use of a "Thorp" plate which has regularly spaced apertures 26. The plate 24 is attached to the bone by fasteners which comprise a titanium cylinder 28 passed through one of the apertures 26 into a bore drilled in the bone, and a screw 30 engaging internally in the cylinder 28 to produce a wedging effect. This arrangement is less prone to loosen than bone screws, and copes well with bone regrowth.

FIG. 5 illustrates in more detail the relationship of the implant, bone and soft tissue.

Figure 5A:
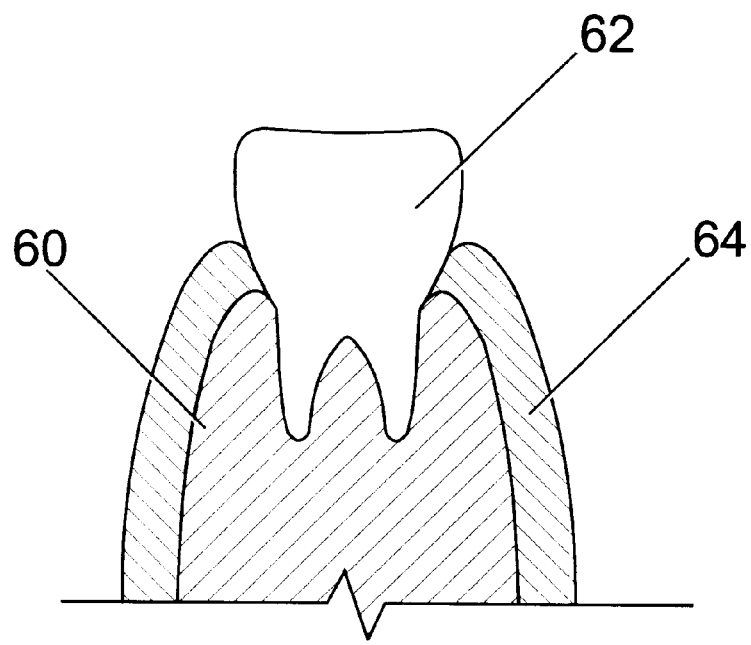
FIGS. 5a and 5b are schematic cross-sections illustrating a healthy jaw and a jaw with an implant.

FIG. 5a shown schematically a healthy jaw including mandible 60, tooth 62 and soft tissue 64.

Figure 5B:
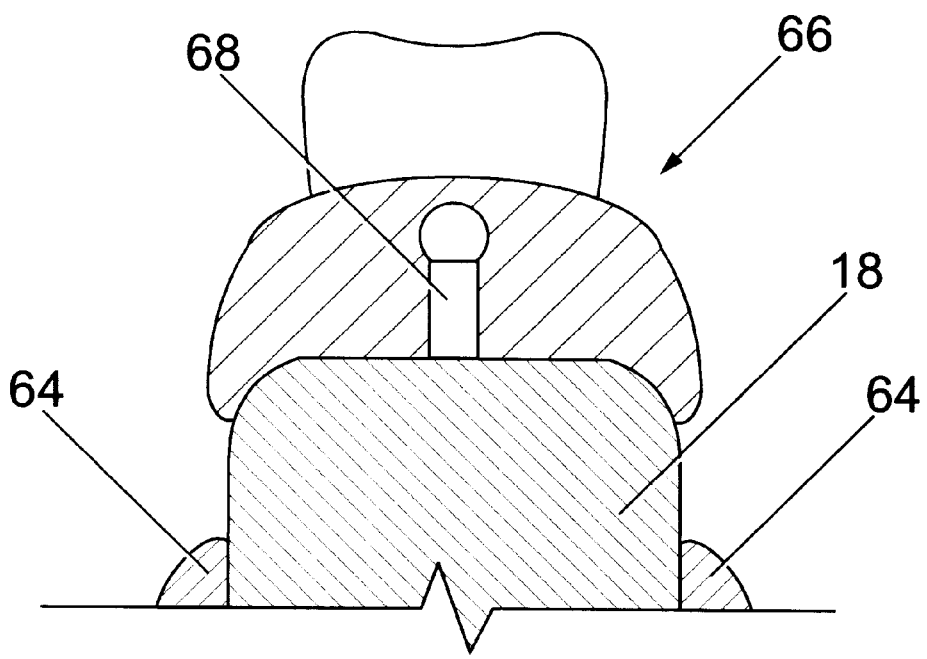

In FIG. 5b, it will be seen that the implant 18 entirely replaces excised bone and soft tissue, without any need to recreate bone or soft tissue. The remaining soft tissue 64 locates on the surface of the implant 18, FIG. 5b also illustrates a denture 66 releasably secured to the implant 18 by engagement with a post 68 upstanding from the body of the implant 18. Posts of this nature are known per se for securing dentures in oral reconstruction.

Figure 6:
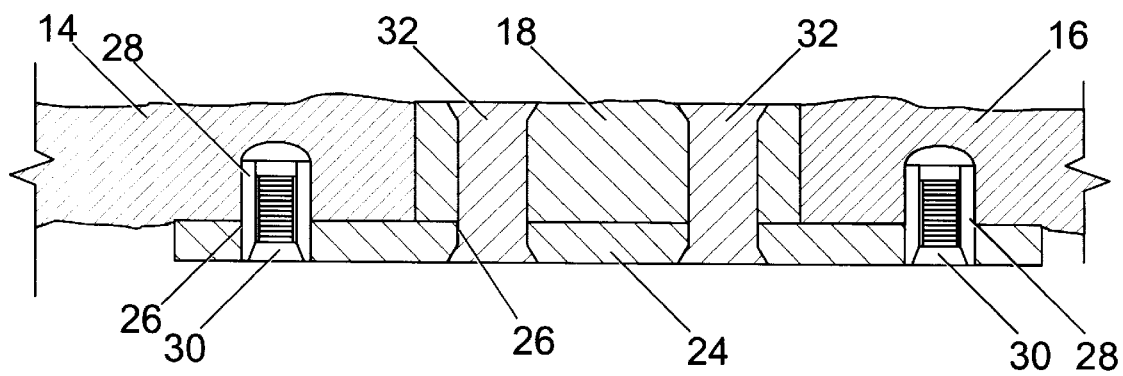
FIG. 6 is a schematic side view of an alternative mounting arrangement.

The implant 18, in the example of FIG. 6, is secured to the plate by titanium rivets 32.

In a modification (not shown), the implant may be made in a modular fashion, with the total volume to be replaced being provided by a number of interfitting parts which may, for example, be secured to a common mounting plate such as the plate 24 of FIG. 6. This arrangement may simplify the surgical procedure n certain cases.

Figure 7A:
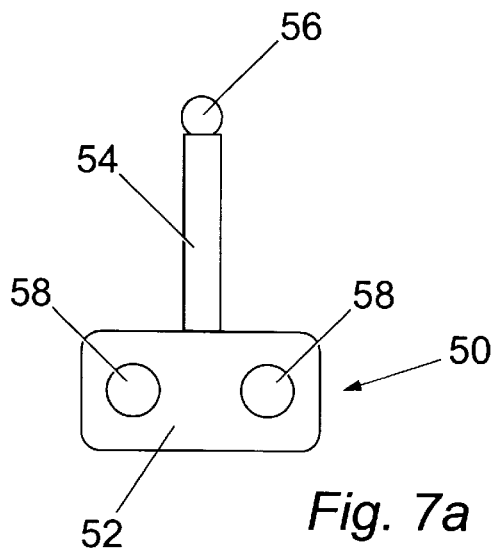
FIGS. 7a, 7b and 7c are respectively side, end and plan views of a connector block embodying a further aspect of the invention.
Figure 7B:
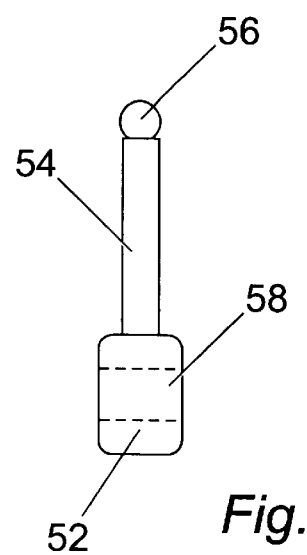
Figure 7C:
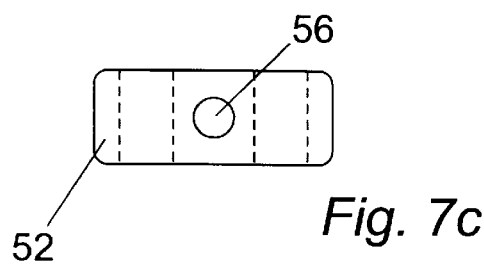

FIG. 7 shows a connector block 50 which may be used with the embodiments described above, or for other applications.

The block 50, which is machined from solid titanium, has a rectangular body 52 with an upstanding post 54. The top of the post 54 is formed into a part-sphere 56 for attachment of dentures, bridgework, etc.

The body 52 is formed with parallel, circular passages 58 which enable the connector block 50 to be connected to an apertured device such as a "Thorp" plate by rivets, as in FIG. 6.

The part-sphere 56 is suitable for certain known types of connection. It may be replaced by alternative formations at the top of the post, for example for cooperation with screw-type connections.

Modifications may be made to the foregoing embodiments within the scope of the invention.

For example, the invention may be applied to disorders of growth such as the situation where one cheekbone fails to grow and is sunken with regard to the other cheekbone. In this case, an implant can be produced by the techniques described but based on data from the normal cheekbone, and secured to the defective bone as an onlay.

In another example, a tumour of leg tissue may be excised and the requisite volume filled by an implant secured to a leg bone.

In both of these cases, the tissues overlying the site would be separated to allow insertion of the implant, and then reclosed. The implant thus does not penetrate the body surface post-operatively, and biocompatible materials other than titanium may be used.

What is claimed is:

1. A method of making a prosthetic implant comprising the steps of:

obtaining a set of data defining body parts of interest from a patient in three dimensions, using said set of date to create a three dimensional model of at least part of the body parts of interest, and using the three dimensional model to develop and fit to size a prosthetic implant which entirely replaces body parts which are missing or are to be excised from the patient and which includes a body surface of skin and mucous membrane, and wherein the prosthetic implant extends through the skin or mucous membrane.

2. A method of treating damaged, diseased or missing body parts having sound adjacent bone structures which comprises excising damaged or diseased body parts and selected adjacent parts, and replacing excised or missing parts entirely by a prosthetic implant secured to the sound adjacent bone structures.

3. The method of claim 2, in which both bone and soft tissue are replaced by a single prosthetic implant made of a material having a surface, wherein soft tissue is capable of growing onto the surface of said material in a manner to prevent the incursion of infection.

4. The method of claim 3, in which said material is titanium.

5. The method of claim 2, carried out by obtaining a set of data defining the body parts of interest in three dimensions, using said set of data to create a three dimensional model of at least part of the body parts of interest, and using the model to develop and fit to size the prosthetic implant prior to surgery.

6. The method of claim 1, in which said body surface is the palate or nasal cavity.

7. The method of claim 1, in which the set of data defining the body parts of interest is produced by CAT scanning.

8. The method of claim 7, in which the data resulting from the CAT scanning is manipulated by computer.

9. The method of claim 8, in which the data is manipulated to derive from a CAT head scan a set of data defining three dimensionally only the bony structures of a skull.

10. The method of claim 9, in which a three dimensional model may conveniently is produced from aid data by stereolithography.

11. The method of claim 1, wherein said prosthetic implant is made of titanium.

12. A prosthetic implant to entirely replace body parts which are missing or are to be excised from a patient and which includes a body surface of skin and mucous membrane, and wherein the prosthetic implant is capable of extending through the skin or mucous membrane, said implant being obtained using a method comprising the steps of:

obtaining a set of data defining body parts of interest in three dimensions, using said set of data to create a three dimensional model of at least part of the body parts of interest, and using the three dimensional model to develop and fit to size the prosthetic implant; and said prosthetic implant is provided with mechanical attachment for the releasable attachement of a further prosthetic device.

13. The prosthetic implant of claim 12, provided with mechanical attachment means for the releasable attachment of a denture.

14. The prosthetic implant of claim 12, wherein said prosthetic implant is made of titanium.

15. The prosthetic implant of claim 12, wherein said mechanical attachment means for the releasable attachment of a further prosthetic device comprises a connector block, said connector block comprising a body and a post extending from the body, the post being formed with passages for rivets for attachment to a surgical plate.

16. The prosthetic implant of claim 15, wherein the body of said connector block is rectangular and wherein said connector block is formed integrally from titanium.

\* \* \* \* \*